United States Patent [19]

O'Brien, Patrick M. et al.

[11] Patent Number: 5,106,873
[45] Date of Patent: Apr. 21, 1992

[54] ACAT INHIBITORS

[75] Inventors: Patrick M. O'Brien, Northville; Drago R. Sliskovic; Michael W. Wilson, both of Ypsilanti, all of Mich.

[73] Assignee: Warner-Lambert Company, Morris Plains, N.J.

[21] Appl. No.: 543,894

[22] Filed: Jun. 26, 1990

[51] Int. Cl.$^5$ ............................................. A61K 31/17
[52] U.S. Cl. .................... 514/596; 514/561; 514/562; 514/565; 514/566; 514/585; 514/586; 514/587; 514/597; 514/598; 560/18; 560/21; 560/34; 562/435; 562/437; 562/438; 562/439; 564/48; 564/50; 564/52; 564/53; 564/54; 564/27; 564/28; 564/29; 546/337
[58] Field of Search ................. 564/48; 514/596; 546/337

[56] References Cited

U.S. PATENT DOCUMENTS

| | | | |
|---|---|---|---|
| 2,762,842 | 9/1956 | Hafliger et al. | 564/48 |
| 4,224,242 | 9/1980 | Sulkowski et al. | 564/48 |
| 4,397,868 | 8/1983 | DeVries | 564/48 |
| 4,437,880 | 3/1984 | Takahashi et al. | 564/48 |
| 4,473,579 | 9/1984 | DeVries et al. | 564/48 |

FOREIGN PATENT DOCUMENTS

| | | | |
|---|---|---|---|
| 0344425 | 12/1989 | European Pat. Off. | 564/48 |
| 1140507 | 6/1986 | Japan | 71/120 |
| 1161252 | 7/1986 | Japan | 514/596 |
| 8102156 | 8/1981 | PCT Int'l Appl. | 71/120 |
| 0792854 | 6/1985 | U.S.S.R. | 71/120 |

Primary Examiner—Allen J. Robinson
Assistant Examiner—S. Kumar
Attorney, Agent, or Firm—Ruth H. Newtson

[57] ABSTRACT

This invention relates to novel compounds which are ACAT inhibitors rendering them useful in lowering blood cholesterol levels. The compounds contain two urea or thiourea, amide, or amine moieties or combinations of said moieties and have the following general formula:

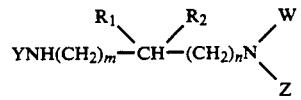

wherein m and n are zero or one, W and YNH and

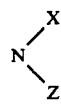

form the urea, thiourea, amide or amine moieties; and $R_1$ and $R_2$ are hydrogen or a hydrocarbon radical.

11 Claims, No Drawings

ACAT INHIBITORS

BACKGROUND OF THE INVENTION

This invention relates to chemical compound having pharmacological activity, to pharmaceutical compositions which include these compounds, and to a pharmaceutical method of treatment. More particularly, this invention concerns certain novel compounds which inhibit the enzyme acylcoenzyme A: cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which could be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

The present invention provides a class of compounds which have acyl-CoA: cholesterol acyltransferase (ACAT) inhibitory activity and intermediates useful in preparing said compounds having the following structure:

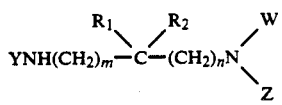

wherein each of m and n is zero or one with the proviso that the sum of m and n is one; wherein (a) each of $R_1$ and $R_2$ is selected from hydrogen, a straight or branched alkyl group having from one to six carbon atoms, or an alkyl group having from one to six carbon atoms wherein the terminal carbon atom is substituted with a hydroxy group with the proviso that one of $R_1$ and $R_2$ is other than hydrogen; or b) $R_1$ is hydrogen and $R_2$ is a cycloalkyl group having from three to six carbon atoms; or (c) $R_1$ is a straight or branched alkyl group having from one to six carbon atoms or an alkyl group having from one to six carbon atoms wherein the terminal carbon atom is substituted with a hydroxy group, and $R_2$ is (i) phenyl $(CH_2)_p$- wherein p is zero or one and wherein the phenyl moiety is unsubstituted or is substituted with from 1 to 3 substituents selected from alkyl having from 1 to 6 carbon atoms and which is straight or branched, alkoxy having from 1 to 6 carbon atoms and which is straight or branched; phenoxy, hydroxy, fluorine, chlorine, bromine, nitro, trifluoromethyl, -COOH, -COOalkyl wherein alkyl has from 1 to 4 carbon atoms -$NR_3R_4$ wherein $R_3$ and $R_4$ are independently hydrogen or alkyl of from 1 to 4 carbon atoms;

(ii) 1- or 2-naphthyl which is unsubstituted or substituted with from one to three substituents selected from: alkyl having from 1 to 6 carbon atoms and which is straight or branched; alkoxy having from 1 to 6 carbon atoms and which is straight or branched; hydroxy, fluorine, chlorine, bromine, nitro, trifluoromethyl, —COOH, —COOalkyl wherein alkyl has from 1 to 4 carbon atoms -$NR_3R_4$ wherein $R_3$ and $R_4$ are as defined above;

(iii) a 5- or 6- membered monocyclic or fused bicyclic heterocycle containing at least one to four nitrogen, oxygen, or sulfur atoms in at least one ring member; or (d) $R_1$ is hydrogen, a straight or branched alkyl group having from one to six carbon atoms, or an alkyl group having from 1 to 6 carbon atoms wherein the terminal carbon atom is substituted with a hydroxy group, and $R_2$ is an amino acid residue selected from

 (i)

 (ii)

 (iii)

 (iv)

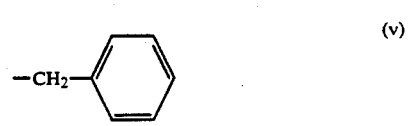 (v)

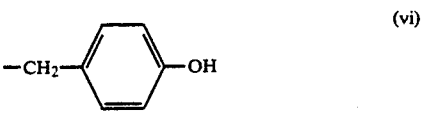 (vi)

—CH₂COOH (vii)

—(CH₂)₂COOH (viii)

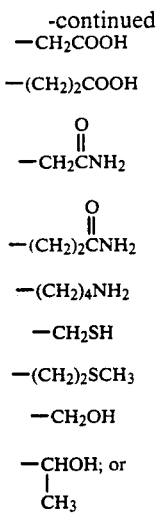

—CH₂CNH₂ (ix)

—(CH₂)₂CNH₂ (x)

—(CH₂)₄NH₂ (xi)

—CH₂SH (xii)

—(CH₂)₂SCH₃ (xiii)

—CH₂OH (xiv)

—CHOH; or (xv)
 |
 CH₃

(e) $R_1$ and $R_2$ taken together with the carbon atom to which they are attached form a carbocyclic ring having from three to six carbon atoms; wherein y and Z are independently selected from:

(a) hydrogen

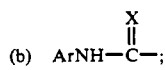

(b) ArNH—C—;

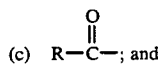

(c) R—C—; and (d) R—CH₂;

wherein X is oxygen or sulfur; wherein Ar is selected from:

(a) phenyl which is unsubstituted or is substituted with from 1 to 3 substituents selected from alkyl having from 1 to 6 carbon atoms and which is straight or branched, alkoxy having from 1 to 6 carbon atoms and which is straight or branched, phenoxy, hydroxy, fluorine, chlorine, bromine, nitro, trifluoromethyl, —COOH, —COOalkyl wherein alkyl has from 1 to 4 carbon atoms -NR₃R₄ wherein $R_3$ and $R_4$ are independently hydrogen or alkyl of from 1 to 4 carbon atoms; and (b) 1- or 2-naphthyl which is unsubstituted or substituted with from one to three substituents selected from: alkyl having from 1 to 6 carbon atoms and which is straight or branched; alkoxy having from 1 to 6 carbon atoms and which is straight or branched, hydroxy, fluorine, chlorine, bromine, nitro, trifluoromethyl, —COOH, —COOalkyl wherein alkyl has from 1 to 4 carbon atoms, -NR₃R₄ wherein $R_3$ and $R_4$ are as defined above;

wherein R is selected from:

(a) a straight or branched hydrocarbon chain having from 1 to 20 carbon atoms and which is saturated or contains from 1 to 3 double bonds;

(b) a straight or branched hydrocarbon chain having from 1 to 6 carbon atoms wherein the terminal carbon atom is substituted with chlorine; fluorine; bromine; straight or branched lower alkoxy having from 1 to 4 carbon atoms; straight or branched thioalkoxy having from 1 to 4 carbon atoms; a —COOR₅ group wherein $R_5$ is hydrogen or a straight or branched alkyl having from 1 to 4 carbon atoms; an -NR₆R₇ group wherein $R_6$ and $R_7$ are independently hydrogen or lower alkyl having from 1 to 4 carbon atoms wherein said alkyl is unsubstituted or is substituted with hydroxy, or wherein -NR₆R₇ taken together form a monocyclic heterocyclic group selected from pyrrolidino, piperidino, piperazino or piperazino substituted in the 4-position with a lower alkyl having from 1 to 4 carbon atoms or -COOR₅ wherein $R_5$ has the meaning defined above; and (c) a 5- or 6-membered monocyclic or fused bicyclic heterocycle containing at least one to four nitrogen, oxygen or sulfur atoms in at least one ring member;

(d) the group

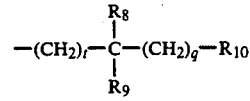

wherein t is zero to 4; q is zero to 4 with the proviso that the sum of t and q is not greater than 5; $R_8$ and $R_9$ are independently selected from hydrogen or alkyl having from 1 to 6 carbon atoms, or when $R_8$ is hydrogen, $R_9$ can be the same as $R_{10}$; and $R_{10}$ is phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, —COOH, COOalkyl wherein alkyl has from 1 to 4 carbon atoms, or NR₆R₇; wherein $R_6$ and $R_7$ have the meanings defined above; and (e) phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, —COOH, COOalkyl wherein alkyl has from 1 to 4 carbon atoms, or NR₆R₇ having the meanings defined above; wherein W is selected from:

(a) hydrogen (b) a straight or branched hydrocarbon chain having from 1 to 20 carbon atoms and which is saturated or contains from 1 to 3 double bonds;

(c) a straight or branched hydrocarbon chain having from 1 to 6 carbon atoms wherein the terminal carbon atom is substituted with chlorine; fluorine, bromine, straight or branched lower alkoxy having from 1 to 4 carbon atoms; straight or branched thioalkoxy having from 1 to 4 carbon atoms; a —COOR₅ group wherein $R_5$ is hydrogen or a straight or branched alkyl having from 1 to 4 carbon atoms; an -NR₆R₇ group wherein $R_6$ and $R_7$ are independently hydrogen or lower alkyl having from 1 to 4 carbon atoms wherein said alkyl is unsubstituted or is substituted with hydroxy, or wherein -NR₆R₇ taken together form a monocyclic heterocyclic group selected from pyrrolidino, piperidino, piperazino or piperazino substituted in the 4-position with a lower alkyl having from 1 to 4 carbon atoms or —COOR₅ wherein $R_5$ has the meaning defined above;

(d) the group

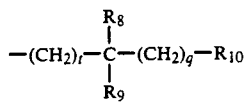

wherein t is zero to 4; q is zero to 4 with the proviso that the sum of t and q is not greater than 5; $R_8$ and $R_9$ are independently selected from hydrogen or alkyl having from 1 to 6 carbon atoms, or when $R_8$ is hydrogen, $R_9$ can be the same as $R_{10}$; and $R_{10}$ is phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, —COOH, COOalkyl wherein alkyl has from 1 to 4 carbon atoms, or $NR_6R_7$ wherein $R_6$ and $R_7$ have the meanings defined above; and (e) phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, —COOH, COOalkyl wherein alkyl has from 1 to 4 carbon atoms, or $NR_6R_7$ wherein $R_6$ and $R_7$ have the meanings defined above; or a pharmaceutically acceptable salt and N-oxides thereof; with the provisos:

(a) when both Z and W are the group

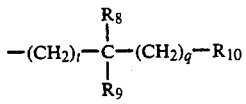

$R_9$ and $R_{10}$ are not the same; and (b) each of Y, Z, and W are not hydrogen at the same time.

In addition to being pharmaceutically useful compounds, the compounds of Formula I wherein Y, Z, or W is hydrogen also can be intermediates to prepare other compounds of Formula I which will be apparent from the general description of the preparation of the compounds and the specific examples.

DETAILED DESCRIPTION OF THE INVENTION

The present invention provides a novel class of compounds which contain moieties selected from amine, amide, urea, and thiourea groups which are ACAT inhibitors rendering them useful in treating hypercholesterolemia and atherosclerosis.

Illustrative examples of straight or branched saturated hydrocarbon chains having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

Illustrative of straight or branched thioalkoxy groups having from 1 to 4 carbon atoms are methylthio, ethylthio, n-propylthio, isopropylthio, and butylthio. The thioalkoxy group may also be referred to as alkylthio.

A 5- or 6- membered monocyclic or fused bicyclic heterocycle is a monocyclic or fused bicyclic aromatic ring containing at least one to four hetero atoms in at least one ring, such as nitrogen, oxygen, sulfur, or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, oxazolyl, isoxazolyl, triazolyl, tetrazolyl, imidazolyl, benzothiazolyl, indolyl, quinolinyl, isoquinolinyl, or N-oxides of heterocycle containing a nitrogen atom.

More specifically, such a heterocycle may be a 2-or 3-thienyl; 2- or 3-furanyl; 2-, 3-, or 4-pyridyl or -pyridyl-N-oxide; 2-, 4-, or 5-pyrimidinyl; 3- or 4-pyridazinyl; 2-pyrazinyl; 2- or 3-pyrrolyl; 3-, 4-, or 5-pyrazolyl, 3-, 4-, or 5-isoxazolyl; 3-, 4-, or 5-isoxazolyl; 3-, 4-, or 5-oxazolyl; 3-, 4-, or 5-isothiazolyl; 5-tetrazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

Illustrative examples of straight or branched alkyl groups having from 1 to 6 carbon atoms include methyl, ethyl, n-propyl, n-butyl, isopropyl, and tert-butyl.

The group phenyl$(CH_2)_p$- wherein p is zero or one represents phenyl or benzyl wherein the phenyl ring or the aromatic ring of the benzyl group is unsubstituted or is substituted with from one to three substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, —COOalkyl wherein the alkyl moiety has from 1 to 4 carbon atoms or -$NR_3R_4$ wherein each of $R_3$ and $R_4$ is selected from hydrogen or an alkyl group having from 1 to 4 carbon atoms.

Cycloalkyl groups having from 3 to 6 carbon atoms include cyclopropyl, cyclobutyl, cyclopentyl, and cyclohexyl.

It is apparent from Formula I that compounds of the present invention wherein both Y and Z are

are bis-urea or bis-thiourea derivatives, or wherein both Y and Z are

are bis-amide derivatives, or wherein both Y and Z are R-$CH_2$- are bis-amine derivatives. It is also apparent form Formula I that the substituent groups Y and Z may be different in which case the compounds of the present invention are urea-amide or thiourea-amide compounds, or are urea-amine or thiourea-amine compounds or are amide-amine compounds.

In one preferred embodiment of the present invention at least one of the groups Y or Z represents a urea or thiourea moiety, i.e., Y or Z is the group $$\text{ArNHC(X)}-$$

In another preferred embodiment of the present invention at least one of Y or Z is a urea moiety, i.e., the group $$\text{ArNHC(X)}-$$

wherein X is oxygen. Compounds of the following general Formula II wherein each of Y and Z represents the group $$\text{ArNHC(X)}-$$

represent preferred compounds of the present invention:

$$\text{ArNHC(X)NH(CH}_2)_m-\underset{R_1}{\overset{R_2}{C}}-(CH_2)_n-\underset{W}{N}-C(X)NHAr} \quad \text{Formula II}$$

Compounds of Formula II wherein X is oxygen are more preferred. Another preferred embodiment of the present invention are compounds wherein one of Y or Z represents $$\text{ArNHC(X)}-$$

and the other of Y or Z represents $$\text{R}-\overset{O}{\underset{\|}{C}}-$$

which compounds are depicted by the following Formulas III and IV:

$$\text{ArNHC(X)NH}-(CH_2)_m-\underset{R_1}{\overset{R_2}{C}}-(CH_2)_n-\underset{W}{N}-C(O)R} \quad \text{Formula III}$$

$$\text{RC(O)NH(CH}_2)_m-\underset{R_1}{\overset{R_2}{C}}-(CH_2)_n-\underset{W}{N}-C(X)NHAr} \quad \text{Formula IV}$$

Compounds of Formula II and IV wherein X is oxygen are more preferred. Another preferred embodiment of the present invention are compounds wherein one of Y and Z represents $$\text{ArNHC(X)}-$$

and the other of Y and Z represents R-CH$_2$- which compounds are depicted by the following Formulas V and VI:

$$\text{NHArC(X)NH}-(CH_2)_m-\underset{R_1}{\overset{R_2}{C}}-(CH_2)_n-\underset{W}{N}-CH_2R} \quad \text{Formula V}$$

$$\text{RCH}_2\text{NH(CH}_2)_m-\underset{R_1}{\overset{R_2}{C}}-(CH_2)_n-\underset{W}{N}-C(X)NHAr} \quad \text{Formula VI}$$

Of the compounds represented by Formulas II through VI the compounds for Formulas II, III, and V are more preferred and within these compounds those wherein X is oxygen are more preferred. Other preferred compounds of this invention are those wherein Ar is phenyl or substituted phenyl and more preferably wherein Ar is phenyl substituted on the 2,6-positions. Other preferred compounds of this invention are those wherein W is hydrogen.

Pharmaceutically acceptable salts of the compounds of Formula I are also included as a part of the present invention.

The acid salts may be generated from the free base by reaction of the latter with one equivalent of a suitable nontoxic, pharmaceutically acceptable acid, followed by evaporation of the solvent employed for the reaction and recrystallization of the salt if required. The free base may be recovered from the acid salt by reaction of the salt with an aqueous solution of a suitable base such as sodium carbonate, sodium bicarbonate, potassium carbonate, sodium hydroxide, and the like.

Suitable acids for forming acid salts of the compounds of this invention include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically acceptable salts is well known to practitioners of the pharmaceutical formulation arts (see, for example, Stephen N. Berge, et al, *J Pharm Sciences*, 66:1-19 (1977)).

The compounds of the present invention may also exist in different stereoisomeric forms by virtue of the presence of asymmetric centers in the compound. The present invention contemplates all stereoisomeric forms of the compounds as well as mixtures thereof, including racemic mixtures.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field, F. J. and Salone, R. G., Biochemica et Biophysica, 712:557-570 (1982). The test assesses the ability of a test compound to inhibit the acylation of cholesterol by oleic acid by measuring the amount of radiolabeled cholesterol cleate formed from radiolabeled oleic acid in a tissue preparation containing rabbit intestinal microsomes.

The data appear in Table 1 where they are expressed in $IC_{50}$ values; i.e., the concentration of test compound required to inhibit 50% expression of the enzyme.

TABLE 1

| Compound of Example | $IC_{50}$ ($\mu$M) |
|---|---|
| 1 | 0.61 |
| 2 | 2.50 |
| 3 | 0.25 |
| 4 | 0.096 |
| 5 | 0.51 |
| 6 | 0.057 |
| 7 | 0.49 |
| 8 | 0.085 |
| 9 | 0.27 |
| 10 | 0.41 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal, chow diet was then replaced with the PCC diet with either 1% or 0.5% cholic acid, as indicated. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2.

TABLE 2

| Compound of Example | % Change (mg/dl) |
|---|---|
| 6 | −25 |
| 7 | −31 |
| 8 | −17 |
| 9 | −33 |
| 10 | −46 |

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets are also included. Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of this invention are prepared by procedures generally well known in the art. Two general methods for preparing compounds of Formula I are set forth in Chart I and Chart II hereof. In Chart I the various symbols R, Ar, and X have the meanings defined in Formula I. $R_{11}$ and $R_{12}$ are the same as definitions (a), (b), (c), and (e) for $R_1$ and $R_2$ in Formula I. In Chart II the various symbols Ar, R, $R_1$, $R_2$, and X have the same meanings as defined in Formula I, and BOC is tertiary butoxycarbonyl. Chart III hereof sets forth the general scheme for the preparation of compounds (9) in Chart II. It is apparent from general Formula I and Charts I and II that the compounds of the present invention contain various combinations of urea, thiourea, amide, and amine groups. It is also apparent from Charts I and II that the order in which the various amide, amine, urea, and thiourea groups are incorporated into the final products may vary and can be manipulated easily by one skilled in the art.

Referring to Chart I the amino nitrile (2) is prepared via a Strecker synthesis by treating an appropriate aldehyde or ketone (1) with sodium cyanide, ammonium chloride, and ammonium hydroxide in a lower aqueous alcohol, such as, aqueous methanol at a temperature range from 50° C. to 75° C. for 1 to 24 hours. The amino nitrile (2) may be treated with an acylating agent, an alkylating agent, or with an appropriate isocyanate or thioisocyanate as depicted in Chart I to give the nitriles represented by formulas (3), (4), and (5). The nitriles are then reduced using Raney nickel in methanolic ammonia at 50 psi or by using palladium on charcoal in methanol/sulfuric acid to give the amines depicted by formulas (6), (7), and (8). In referring to Chart II the diamine (9) wherein one of the amine groups is protected with an easily removed protecting group such as tertiary butoxycarbonyl is treated with an appropriate isocyanate, thioisocyanate, alkylating agent, or acylating agent to give the amine protected isocyanate or thioisocyanate (10), amide (11) or amine (12). Compounds (10), (11), and (12) are then deprotected using HCl gas in dichloromethane at room temperature to give the free amine compounds (13), (14), and (15). In referring again to Chart I the amino nitrile (2) may be resolved by treatment with D or L tartaric acid as generally described in J. Med. Chem. 28(9):1280 (1985) by adding a methanolic solution of tartaric acid to a solution of the amino nitrile in benzene-methanol (4:1), filtering the precipitate, washing with benzene-methanol (2:1), and recrystallizing from methanol. When the resolved amino nitrile is treated as depicted in Chart I and as described herein the corresponding resolved final products of Formula I are obtained.

It is readily apparent from Charts I and II that compounds (6), (7), (8), (13), (14), and (15) can be further alkylated, acylated, or treated with an appropriate isocyanate or thioisocyanate to give the compounds of Formula I. To form compounds containing a urea or thiourea moiety the appropriate amine is treated with an aryl isocyanate or an aryl thioisocyanate of the formula ArNCX wherein Ar and X have the meanings defined in Formula I at room temperature in methylene chloride, ethyl acetate, tetrahydrofuran, or acetonitrile. To form compounds containing an amide moiety the appropriate amine is treated with an acid anhydride of the formula $(RCO)_2O$ wherein R has the meaning defined in Formula I. Additionally, an appropriate acid, $RCO_2H$ or acid halide RCOhalo wherein halo is, e.g., chlorine, may also be used. The reaction is carried out at room temperature in tetrahydrofuran, methylene chloride, or chloroform and in the presence of triethylamine. In preparing compounds wherein R is heteroaryl an appropriate heteroarylcarboxylic acid is used with a coupling agent such as carbonyldiimidazole in tetrahydrofuran or dicyclohexylcarbodiimide in methylene chloride.

The amine containing compounds are formed by reducing the corresponding amide via a metal (aluminum) hydride reduction at reflux in toluene or by alkylating a primary or secondary amine-containing compound. Alkylation is achieved by reacting a primary or secondary amine compound with an aldehyde of the formula WCHO wherein W has the meaning defined in Formula I in a lower alcohol such as methanol in the presence of sodium sulfate or calcium sulfate to give the corresponding imine. This reaction may require heating if hindered amines are used. The imine is reduced to the amine using a metal hydride reducing agent such as sodium borohydride in tetrahydrofuran at room temperature. This alkylation may also be achieved using a suitable halide alkylating agent in methylene chloride or tetrahydrofuran using triethylamine as base. When alkylating a primary or secondary amine as depicted in Charts I and II to form compounds of Formula I wherein W is phenyl or a substituted phenyl group the most suitable alkylating agent is the aldehyde WCHO wherein W is phenyl or substituted phenyl.

Compounds of Formula I wherein R represents an alkyl group having from one to six carbon atoms wherein the terminal carbon is substituted with halogen, methoxy, or $NR_6R_7$ are prepared by acylating the appropriate amine using ω-bromoacyl chloride to afford a compound wherein R is $-(CH_2)_mBr$ wherein m is an integer of from one to six. The ω-bromoalkyl containing compound can be subjected to various nucleophilic substitutions to give the corresponding compounds wherein the terminal carbon is substituted with alkoxy, thioalkoxy, $NR_6R_7$, or other halogen atoms. The alkoxy or thioalkoxy-containing compounds are obtained by treating the bromo compound with a suitable alkoxide or thioalkoxide in a lower alcoholic solvent. The $NR_6R_7$ containing compounds are obtained, e.g., by treating the bromo compound with ammonia gas to give the corresponding ω-$NH_2$ compound, or with dimethylamine gas to give the ω-$N(CH_3)_2$ compound or with an excess of an appropriate amine in a lower alcohol solvent at elevated temperature, e.g., 80° to 95° C. to give the corresponding ω-$NR_2R_3$-containing compounds. To obtain compounds wherein the terminal carbon is substituted with a —COORs group the ω-bromo compound is treated with magnesium metal in ether at 0° C. to form a Grignard reagent which is treated with solid $CO_2$ to give the ω-COOH compound which is esterified at room temperature using a lower alcohol and a trace of mineral acid.

In Chart III the general procedure for preparing the protected diamine compound (9) used in Chart II is depicted. The BOC-protected amino acid ester (16) is treated with lithium aluminum hydride in tetrahydrofuran or diethyl ether at a temperature ranging from 0° C. to 25° C. to give the corresponding alcohol (17). The alcohol (17) is converted to the mesylate (18) by treatment with methanesulfonyl chloride in dichloromethane, pyridine, or chloroform at a temperature of from −25° C. to 0° C. using triethylamine as base followed by a nucleophilic substitution reaction using sodium azide in dimethylformamide at 60° C. to 80° C. The azide (19) is reduced to the corresponding amine (9) using lithium aluminum hydride in tetrahydrofuran or diethyl ether at a temperature ranging from 0° C. to 25° C.

The amino acid ester compounds (16) and the aldehyde or ketones compounds (1) are commercially available or are prepared by procedures generally well known in the art.

The procedure outlined in Chart I gives the final products in the form of a racemic mixture. The procedure outlined in Chart II gives the final products as a racemic mixture or the individual enantiomers depending on the form of the starting material (16) used in Chart III. The enantiomers of compounds (16) are commercially available or may be prepared by well known procedures.

EXAMPLE 1

(±)-N-[2-[[[[2,6-bis(1-methylethyl)phenyl]amino]carbonyl]amino]-1-methyl-1-(2-pyridinyl)ethyl]-4-methoxybenzamide monohydrochloride (a)

N-[1-cyano-1-(2-pyridinyl)ethyl]-4-methoxygenzamide

2-Acetylpyridine (10.0 g, 0.0825 mole) was added to 50° C. solution of sodium cyanide (4.0 g, 0.0825 mole) ammonium chloride (4.9 g, 0.0908 mole), and ammonium hydroxide (2.9 g, 0.0825 mole ) in water (22 mL) and methanol (15 mL). The resulting mixture was stirred at 50° C. overnight. The mixture was cooled and concentrated under reduced pressure. The residue was dissolved in methylene chloride (40 mL) and washed with water (10 mL) and dried over MgSo4. Filtration and concentration gave a dark red oil which was dissolved in methanol and treated with saturated ethereal HCl. Concentration yielded a low melting solid which was dissolved in tetrahydrofurna (50 mL) and treated sequentially with triethylamine (13.7 g, 0.135 mole) and p-anisoyl chloride (8.4 g, 0.0495 mole) dropwise. The solution was stirred 3 hours at room temperature then diluted with ether (100 mL) and washed with 2M HCl, 1M NaOH, saturated NaCl, and dried over MgSo4. Filtration and concentration of the solvent in vacuo provided a solid which was recrystalized from ethyl acetate/hexane to give 5.2 g of N-[-1-cyano-1-(2-pyridinyl)ethyl]-4-methoxybenzamide, mp 173° C.

(b)

N-[2-amino-1-methyl-1-(2-pyridyl)ethyl]-4-methoxybenzamide

N-[-1-cyano-1-(2-pyridinyl)ehtyl]-4-methoxy-benzamide (4.7 g, 0.0167 mole) was dissolved in 100 mL methanolic ammonia and treated with 1.5 g Raney nickel under 50 psi and warmed to 40° C. for 10 hours. The mixture was filtered and the supernate concentrated in vacuo to yield a pale green oil. The crude product (2.3 g) was used in the next step without further purification.

(c) The benzamide from (b) was dissolved in ethyl acetate (15 mL) and treated with 2,6-diisopropyl phenylisocyanate (1.7 g, 0.0083 mole). The resulting mixture was stirred 2 hours at room temperature then concentrated in vacuo. The residue was dissolved in methanol and treated with saturated ethereal HCl, concentrated in vacuo and crystalized from methanol/ether, and dried overnight in vacuo at 55° C. to yield 2.8 g of (±)-N-[2-[[[[2,6-bis(1-methylethyl)-phenyl]amino]carbonyl]amino]-1methyl-1 -(2-pyridinyl)ethyl]-4-methoxygenzamide, monohydrochloride, mp 154°-158° C.

When in the procedure of Example 1 an appropriate amount of the starting material listed below is substituted for 2-acetylpyridine and the general procedure of Example 1 was followed the products listed below were obtained:

| Example | Starting Material | Product |
|---|---|---|
| 2 | Dimethylketone | N-[2-[[[[2,6-bis(1-methylethyl)phenyl]amino]carbonyl]amino]-1,1-dimethylethyl]-4-methoxybenzamide, 1.15 (12H, broad multiplet, $H_3C$ $CH_3$—); 1.41, 6H, singlet, methyl groups); 3.20-3.25 (4H, multiplet, —C$H_2$—, $H$->-); 3.84 (3H, singlet, —OC$H_3$); 4.75 (1H, broad mult., N$H$); 5.88 (1H, broad mult., N$H$); 6.93-7.86 (7H, multiplet, aromatic); 8.12 (1H, broad mult., N$H$) |
| 3 | Cyclohexylaldehyde | (±)-N-[2-[[[[2,6-bis(1-methylethyl)phenyl]amino]-carbonyl]amino]-1-cyclohexylethyl]-4-methoxybenzamide, mp 231-232° C. |
| 4 | Di n-propyl-ketone | N-[1-[[[[2,6-bis(1-methylethyl)phenyl]amino]carbonyl]amino]methyl]-1-propylbutyl]-4-methoxybenzamide, 0.848 (6H, triplet, CH$_2$C$H_3$); 1.15-1.30 (16H, broad multiplet, —CH$_2$—C$H_2$—$\overset{CH_3}{\underset{H_3C}{\phantom{C}}}$—); 1.66-1.88 (4H, multiplet, —CH$_2$—C$H_2$—); 3.17-3.28 (2H, heptet, $H$->-); 3.38-3.40 (2H, broad doublet, —C$H_2$—); 3.84 (3H, singlet, —OC$H_3$); 4.78 (1H, broad mult., N$H$); 5.88 (1H, broad mult., N$H$); 6.88-7.75 (8H, mult., aromatic, N$H$) |
| 5 | Cyclopentyl-ketone | N-[1-[[[[2,6-bis(1-methylethyl)phenyl]amino]carbonyl]amino]methyl]cyclopentyl]-4-methoxybenzamide, mp 158-159° C. |

EXAMPLE 6

(S)-(—)-N-[2,6-bis(1-methylethyl)phenyl]-N'-[2-[[(4-methoxyphenyl)methyl]amino]-4-methyl-pentyl]urea (a)

(S)-(—)-1,1-Di-methylethyl-(1-hydroxymethyl-3-methylbutyl)carbamate

Lithium aluminum hydride (0.65 g; 0.017 mole) was slurried in THF (60 mL) and cooled to 0° C. under a N$_2$ atmosphere. A solution of S-(—)-2[(1,1-dimethylethoxy)carbonylamino]-4-methylpentanoic acid, methyl ester (3.0 g; 0.012 mole) dissolved in THF (15 mL) was added dropwise and upon completion of the addition the suspension was gradually warmed to room temperature with stirring overnight. The mixture was further cooled to —40° C. and treated with a solution of NaHSO$_4$ (2.1 g; 0.015 mole) in H$_2$O (10 mL), diluted with EtOAc (100 mL), and filtered through celtie. The filtrate was dried over MgSO$_4$, filtered, and concentrated in vacuo leaving an orange syrup. The product was chromatographed using silica gel and Et$_2$O as the eluant. Yield: 2.2 g (84%); oil.

(b) (S)-)—)-1,1-Dimethylethyl [3-methyl-1-((methylsulfonyloxy)methyl)butyl]carbamate The product from (a) above (1.9 g; 8.7 mmole) was dissolved in CH$_2$Cl$_2$ (70 mL), cooled to 0° C., and treated with NEt$_3$ (1.7 g; 17.4 mmole). Soon after, methanesulfonyl chloride (1.06 g; 9.5 mmole) was added at such a rate so as not to exceed a solution temperature of 3° C. The solution was stirred for 45 minutes, treated with aqueous saturated sodium chloride (40 mL), and the layers separated. The organic portion was dried over MgSo₄, filtered, and concentrated to dryness. The residue was triturated with hexane and the resulting solid collected by filtration. Yield: 2.0 g (77%) [α]$_D$23 = −38° (1% CHCl₃).

(c)
(S)-(−)-1,1-Dimethylethyl(1-azidomethyl-3-methyl-butyl)carbamate

The product from (b) above (1.9 g; 6.4 mmole) was dissolved in DMF (20 mL) and treated with NaN₃ (2.0 g; 32 mmole) in one portion. The mixture was heated to 80° C. for over 4 hours, cooled, and diluted with H₂O (40 mL). The product was extracted with two portions of Et₂O. The extracts were combined, dried over MgSO₄, filtered, and concentrated n vacuo leaving a colorless liquid. The product was dissolved in hexane/ethyl acetate (4:1) and chromatographed using hexane/EtOAc as the eluant. Fractions containing the product were combined and concentrated in vacuo leaving a white solid. Yield: 1.2 g (76%) [α]$_D$23 = −50° (1% CHCl₃).

(d) (S)-(−)-1,1-Dimethylethyl (1-aminomethyl-3-methylbutyl)carbamate

Lithium aluminum hydride (0.24 g; 6.4 mmole) was slurried in THF (20 mL) and cooled to 0° C. The suspension was treated with a solution of the carbamate from (c) above (1.1 g; 4.6 mmole) in THF (10 mL) and stirred for 2 hours at 0° C. The mixture was further cooled to −30° C. and a solution of NaHSO₄ (0.6 g; 4.3 mmole) in H₂O (5 mL) was cautiously added and then diluted with EtOAc (50 mL), and filtered through celite. The filtrate was dried over MgSo₄, filtered, and concentrated in vacuo leaving a colorless liquid. Yield: 1.0 g (100%)

(e)
(S)-(−)-1,1-Dimethylethyl[3-methyl-1-[[[[[2,6-bis(1-methylethyl)phenyl]amino]carbonyl]-amino]methyl]-butyl]carbamate.

The carbamate obtained in (d) above (1.0 g; 4.6 mmole) was dissolved in EtOAc (25 mL) and treated with 2,6-diisopropylphenylisocyanate (1.0 g; 5.0 mmole) in one portion. Precipitation occurred after 5 minutes of stirring at room temperature. The mixture was stirred an additional hour and the solid was collected by filtration and washed with hexane. Yield: 1.2 g (63%).

(f)
(S)-(−)-N-[2-Amino-4-methylpentane]-N'-[2,6-bis(1-methylethyl)phenyl]urea The carbamate from (e) above (1.0 g; 2.3 mmole) was slurried in CH₂Cl₂ (125 mL) and treated with HCl (g) in a continuous stream with stirring for over 30 minutes. The solution was concentrated in vacuo leaving a white foam. The HCl salt was triturated with hexane and filtered leaving a white solid (0.85 g). The salt was dissolved in ethyl acetate (25 mL)/CH₃OH (2 mL) and treated with NEt₃. After stirring for 10 minutes, H₂O was added and the layers separated. The organic portion was dried over MgSo₄, filtered, and concentrated in vacuo leaving a white solid. Yield: 0.7 g (100%).

(g)
(S)-(−)-N-[2,6-bis(1-methylethyl)phenyl]-N'-[2-[[(4-methoxyphenyl)methyl]amino]-4-methyl-pentyl]urea The urea from (f) above (0.7 g; 2.1 mmole) was dissolved in CH₃OH (50 mL) and stirred over Na₂SO₄ (2.2 g; ANH) for 10 minutes. 4-Anisaldehyde (0.24 g; 2.1 mmole) was added in one portion and stirred at room temperature overnight. The suspension was concentrated in vacuo and the residue was treated with THF (50 mL). The insoluble material was removed by filtration and to the filtrate was added NaBH₄ (0.39 g) with stirring for 30 minutes. The mixture was treated with H₂O (50 mL) and the product was extracted using two portions of CHCl₃. The organic solution was dried over Na₂SO₄, filtered, and concentrated in vacuo leaving a viscous liquid. The crude product was treated with warm EtOAc hexane and crystalized on standing. Yield: 0.54 g (56%). [α]$_D$23 = −20° (1 6% CHCl₃) of the title compound.

NMR (CDCl₃): δ8.0 (s, 1H), 7.4 (d, 2H), 7.2 (t, 1H), 7.1 (d, 2H), 6.8 (d, 2H), 6.0 (bs, 1H), 4.4 (bs, 1H), 3.6 (s, 3H), 3.5 (m, 1H), 3.2 (m, 4H), 1.4 (m, 2H), 1.3 (m, 2H), 1.2 (bs, 12H), 0.9 (dd, 6H) ppm.

When in the procedure of Example 6, an appropriate amount of the starting material listed below is substituted for (S)-(−)-2[(1,1-dimethylethoxy)carbonylamino]-4-methylpentanoic acid, methyl ester and the general procedure of steps (a) through (g) of Example 6 are followed the products listed below are obtained.

| Example | Starting Material | Product |
| --- | --- | --- |
| 7 | (S)-(−)-2-[(1,1-dimethylethoxy)carbonylamino]-4-methylthiobutyric acid, methyl ester | (S)-(−)-N-[2,6-Bis-(1-methylethyl)-phenyl]-N'-[2-[[(4-methoxyphenyl)-methyl]amino]-4-(methylthio)butyl]urea, mp 96–97° C. |
| 8 | (S)-(−)-2-[(1,1-dimethylethoxy)carbonylamino]-3-methylbutyric acid, methyl ester | (S)-(−)-N[2,6-Bis-(1-methylethyl)-phenyl]-N'-[2-[[(4-methoxyphenyl)-methyl]amino]-3-methylbutyl]urea mp 84–86° C. |
| 9 | (S)-(−)-2-[(1,1-dimethylethoxy)carbonylamino]-3-phenylpropionic acid | (S)-(−)-N-[2,6-Bis-(1-methylethyl)-phenyl]-N'-[2-[[(4-methoxyphenyl)-methyl]amino]-3-phenylpropyl]urea, mp 124–125° C. |

EXAMPLE 10

When in the procedure of Example 6 an appropriate amount of (S)-(−)-2-[(1,1-dimethylethoxy)carbonylamino]-3-phenylpropionic acid is substituted for (S)-(−)-2[(1,1-dimethylethoxy)carbonylamino]-4-methylpentanoic acid, methyl ester and an appropriate amount of 2-hydroxybenzaldehyde is substituted for 4-anisaldehyde and the general procedure of Example 6 was followed (S)-(−)-N-[2,6-bis (1-methylethyl)-phenyl]-N'-[2-[[(2-hydroxyphenyl)methyl]amino]-3-phenylpropylurea was obtained.

NMR (CDCl₃): δ7.4 (T, 1H), 7.3 (M, 7H), 7.1 (T, 1H), 6.9 (D, 2H), 6.8 (D, 1H), 6.7 (T, 2H), 6.0 (BS, 1H), 4.3

(BS, 1H, 3.9 (Q. 2H), 3.3 (M, 4H), 2.9 (M, 1H), 2.6 (D, 2H, 1.2 (D, 12 H) ppm. $[\alpha]_D23 = -10°$ (1% $CHCl_3$).
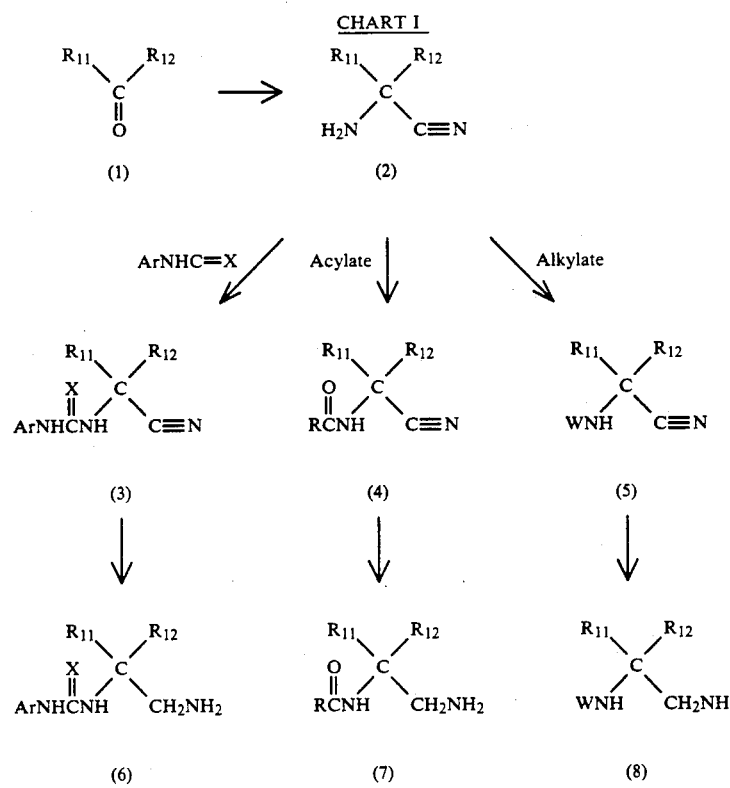
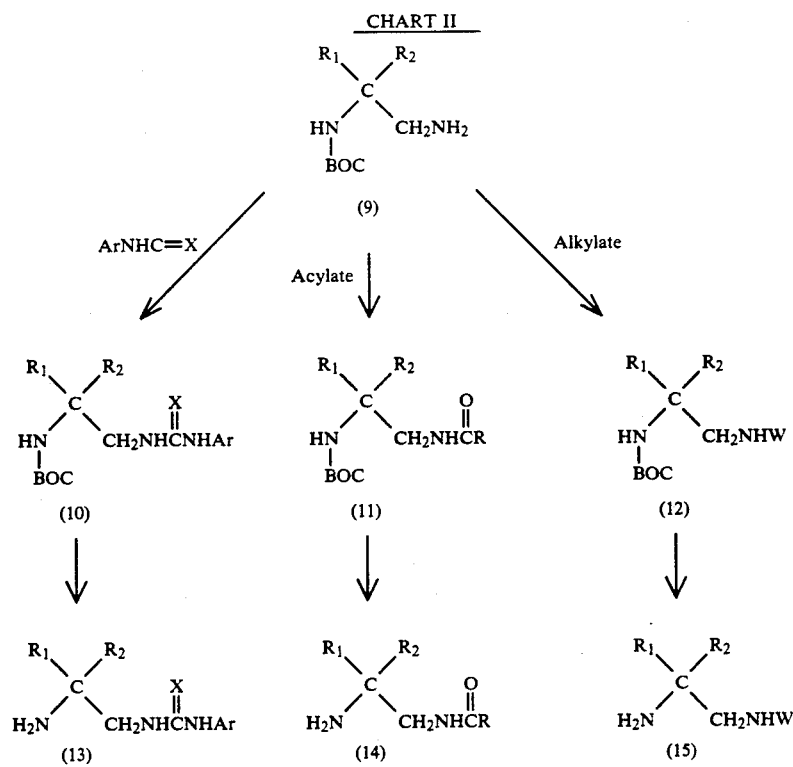

CHART III

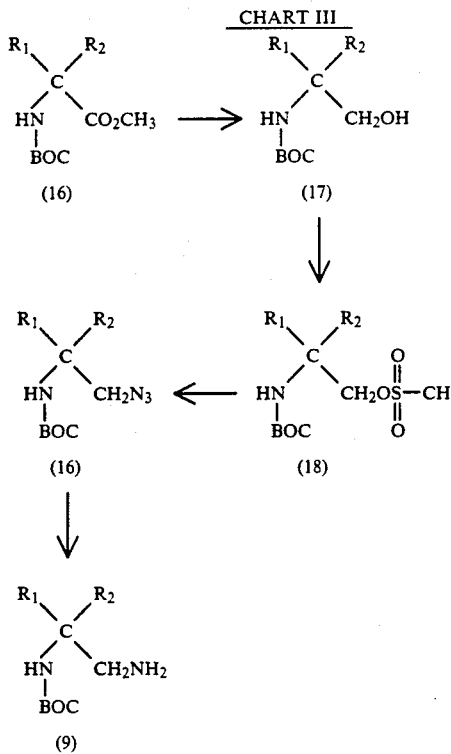

We Claim:
1. A compound of the following Formula I

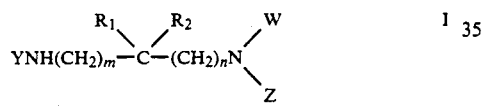

wherein each of m and n is zero or one with the proviso that the sum of m and n is one; wherein
(a) each of $R_1$ and $R_2$ is selected from hydrogen, a straight or branched alkyl group having from one to six carbon atoms, or an alkyl group having from one to six carbon atoms wherein the terminal carbon atom is substituted with a hydroxy group with the proviso that one of $R_1$ and $R_2$ is other than hydrogen; or
(b) $R_1$ is hydrogen and $R_2$ is a cycloalkyl group having from three to six carbon atoms; or
(c) $R_1$ is a straight or branched alkyl group having from one to six carbon atoms or an alkyl group having from one to six carbon atoms wherein the terminal carbon atom is substituted with a hydroxy group, and $R_2$ is
  (i) phenyl $(CH_2)_p$-wherein p is zero or one and wherein the phenyl moiety is unsubstituted or is substituted with from 1 to 3 substituents selected from alkyl having from 1 to 6 carbon atoms and which is straight or branched, alkoxy having from 1 to 6 carbon atoms and which is straight or branched; phenoxy, hydroxy, fluorine, chlorine, bromine, nitro, trifluoromethyl, -$NR_3R_4$ wherein $R_3$ and $R_4$ are independently hydrogen or alkyl of from 1 to 4 carbon atoms; or (ii) 1- or 2-naphthyl which is unsubstituted or substituted with from one to three substituents selected from: alkyl having from 1 to 6 carbon atoms and which is straight or branched; alkoxy having from 1 to 6 carbon atoms and which is straight or branched, hydroxy, fluorine, chlorine, bromine, nitro, trifluoromethyl, -$NR_3R_4$ wherein $R_3$ and $R_4$ are as defined above; or
(d) $R_1$ is hydrogen, a straight or branched alkyl group having from one to six carbon atoms, or an alkyl group having from 1 to 6 carbon atoms wherein the terminal carbon atom is substituted with a hydroxy group, and $R_2$ is an amino acid residue selected from

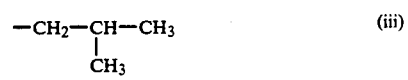
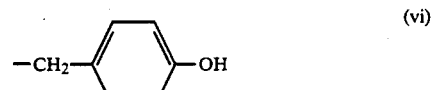

(e) $R_1$ and $R_2$ taken together with the carbon atom to which they are attached form a carbocyclic ring having from three to six carbon atoms; wherein one of Y and Z is

and the other of Y and Z is selected from (a) hydrogen

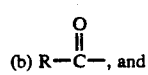, and (c) $RCH_2$—;

wherein X is oxygen; wherein Ar is selected from:
(a) phenyl which is unsubstituted or is substituted with from 1 to 3 substituents selected from: alkyl having from 1 to 6 carbon atoms and which is straight or branched, alkoxy having from 1 to 6 carbon atoms and which is straight or branched; phenoxy, hydroxy, fluorine, chlorine, bromine, nitro, trifluoromethyl, -NR$_3$R$_4$ wherein R$_3$ and R$_4$ are independently hydrogen or alkyl of from 1 to 4 carbon atoms; and (b) 1- or 2-naphthyl which is unsubstituted or substituted with from one to three substituents selected from: alkyl having from 1 to 6 carbon atoms and which is straight or branched, alkoxy having from 1 to 6 carbon atoms and which is straight or branched; hydroxy, fluorine, chlorine, bromine, nitro, trifluoromethyl, -NR$_3$R$_4$ wherein R$_3$ and R$_4$ are as defined above; wherein R is selected from:

(a) a straight or branched hydrocarbon chain having from 1 to 20 carbon atoms and which is saturated or contains from 1 to 3 double bonds;

(b) a straight or branched hydrocarbon chain having from 1 to 6 carbon atoms wherein the terminal carbon atom is substituted with chlorine; fluorine; bromine; straight or branched lower alkoxy having from 1 to 4 carbon atoms; straight or branched thioalkoxy having from 1 to 4 carbon atoms; an -NR$_6$R$_7$ group wherein R$_6$ and R$_7$ are independently hydrogen or lower alkyl having from 1 to 4 carbon atoms wherein said alkyl is unsubstituted or is substituted with hydroxy;

(c) the group

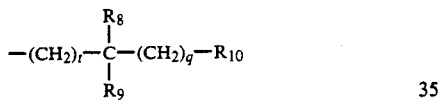

wherein t is zero to 4; q is zero to 4 with the proviso that the sum of t and q is not greater than 5; R$_8$ and R$_9$ are independently selected from hydrogen or alkyl having from 1 to 6 carbon atoms, or when R$_8$ is hydrogen, R$_9$ can be the same as R$_{10}$; and R$_{10}$ is phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, or NR$_6$R$_7$ wherein R$_6$ and R$_7$ have the meanings defined above; and (d) phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, or NR$_6$R$_7$ wherein R$_6$ and R$_7$ have the meanings defined above; wherein W is selected from:

(a) hydrogen (b) a straight or branched hydrocarbon chain having from 1 to 20 carbon atoms and which is saturated or contains from 1 to 3 double bonds;

(c) a straight or branched hydrocarbons chain having from 1 to 6 carbon atoms wherein the terminal carbon atom is substituted with chlorine, fluorine, bromine, straight or branched lower alkoxy having from 1 to 4 carbon atoms; straight or branched thioalkoxy having from 1 to 4 carbon atoms; a -NR$_6$R$_7$ group wherein R$_6$ and R$_7$ have the meanings defined above;

(d) the group

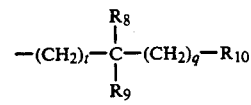

wherein t is zero to 4; q is zero to 4 with the proviso that the sum of t and q is not greater than 5; R$_8$ and R$_9$ are independently selected from hydrogen or alkyl having from 1 to 6 carbon atoms, or when R$_8$ is hydrogen, R$_9$ can be the same as R$_{10}$; and R$_{10}$ is phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, or NR$_6$R$_7$ wherein R$_6$ and R$_7$ have the meanings defined above; and (e) phenyl or phenyl substituted with from 1 to 3 substituents selected from straight or branched alkyl having from 1 to 6 carbon atoms, straight or branched alkoxy having from 1 to 4 carbon atoms, straight or branched thioalkoxy having from 1 to 4 carbon atoms, phenoxy, hydroxy, fluorine, chlorine, bromine, nitro, trifluoromethyl, or NR$_6$R$_7$ wherein R$_6$ and R$_7$ have the meanings defined above; or a pharmaceutically acceptable salt nd N-oxides thereof; with the provisos:

(a) when both R and W are the group

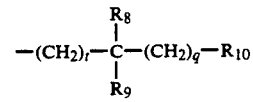

R$_9$ and R$_{10}$ are not the same; and (b) each of Y, Z, and W are not hydrogen at the same time.

2. A compound of claim 1 wherein one of W and Z is hydrogen.

3. A compound of claim 2 wherein Ar is phenyl or substituted phenyl.

4. A compound of claim 3 wherein Ar is phenyl di-substituted in the 2,6-positions.

5. A compound of claim 4 wherein Ar is phenyl di-substituted in the 2,6-positions with a straight or branched alkyl group having from 1 to 6 carbon atoms.

6. A compound of claim 5 wherein the alkyl group is branched and has 3 carbon atoms.

7. A compound of claim 2 wherein Y is RCH$_2$-.

8. A compound of claim 1 which is
(±)-N-[2-[[[[2,6-bis(1-methylethyl)phenyl]amino]carbonyl]amino]-1,1-dimethylethyl]-4-methoxybenzamide;
(±)-N-[2-[[[[2,6-bis(1-methylethyl)phenyl]amino]carbonyl]amino]-1-cyclohexylethyl]-4-methoxybenzamide;

(±)-N-[1-[[[[2,6-bis(1-methylethyl)phenyl]amino]carbonyl]amino]methyl]-1-propylbutyl]-4-methoxybenzamide;

(±)-N-[1-[[[[2,6-bis(1-methylethyl)phenyl]amino]carbonyl]amino]methyl]cyclopentyl]-4-methoxybenzamide;

(±)-N-[2,6-bis(1-methylethyl)phenyl]-N'-[2-[[(4-methoxyphenyl)methyl]amino]-4-methylpentyl]urea;

(±)-N-[2,6-bis(1-methylethyl)phenyl]-N'-[2-[[(4-methoxyphenyl)methyl]amino]-4-(methylthio)-butyl]urea;

(±)-N-[2,6-bis(1-methylethyl)phenyl]-N'-[2-[[(4-methoxyphenyl)methyl]amino]-3-methylbutyl]urea;

(±)-N-[2,6-bis(1-methylethyl)phenyl]-N'-[2-[[(4-methoxyphenyl)methyl]amino]-3-phenylpropyl]urea; or (±)-N-[2,6-bis(1-methylethyl)phenyl]-N'-[2-[[(2-hydroxyphenyl)methyl]amino]-3-phenylpropylurea.

9. A pharmaceutically acceptable salt of a compound of claim 8.

10. A compound of claim 1 which is
(S)-(−)-N-[2,6-bis(1-methylethyl)phenyl]-N'-[2-[[(4-mathoxyphenyl)methyl]amino]-4-(methylpentyl)urea;

(S)-(−)-N-[2,6-bis(1-methylethyl)phenyl]-N'-[2-[2-[(4-methoxyphenyl)methyl]amino]-4-(methylthio)-butyl]urea;

(S)-(−)-N-[2,6-bis(1-methylethyl)phenyl]-N'-[2-[[(4-methoxyphenyl)methyl]amino]-3-methylbutyl]urea;

(S)-(−)-N-[2,6-bis(1-methylethyl)phenyl]-N'-[2-[[(4-methoxyphenyl)methyl]amino]-3-phenylpropyl]urea; or (S)-(−)-N-[2,6-bis(1-methylethyl)phenyl]-N'-[2-[[(2-hydroxyphenyl)methyl]amino]-3-phenylpropylurea.

11. A pharmaceutical composition which comprises a compound of claim 1 and a pharmaceutically acceptable carrier.

* * * * *